US00PP22249P3

(12) United States Plant Patent
Jackson et al.

(10) Patent No.: US PP22,249 P3
(45) Date of Patent: Nov. 15, 2011

(54) JAPANESE MAPLE TREE NAMED 'JN4'

(50) Latin Name: *Acer palmatum*
Varietal Denomination: JN4

(76) Inventors: Ray Jackson, Belvidere, TN (US); Cindy Jackson, Belvidere, TN (US)

( * ) Notice: Subject to any disclaimer, the term of this patent is extended or adjusted under 35 U.S.C. 154(b) by 88 days.

(21) Appl. No.: 12/460,799

(22) Filed: Jul. 24, 2009

(65) Prior Publication Data

US 2011/0023197 P1 Jan. 27, 2011

(51) Int. Cl.
*A01H 5/00* (2006.01)

(52) U.S. Cl. ..... Plt./224

(58) Field of Classification Search ..... Plt./224
See application file for complete search history.

(56) References Cited

U.S. PATENT DOCUMENTS

PP9,697 P 11/1996 Johnston
PP18,728 P3 4/2008 Rumbal

*Primary Examiner* — Kent L Bell
(74) *Attorney, Agent, or Firm* — Polster, Lieder, Woodruff & Lucchesi, LC

(57) ABSTRACT

A Japanese Maple named 'JN4' having persistent red-purple foliage and an early weeping habit, and also capable of being reliably asexually reproduced from chip budding.

3 Drawing Sheets

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to a new and distinct variety of *Acer palmatum,* subsp. *matsumurae* f. *atropurpureum* a Japanese maple tree, referred to by its varietal name 'JN4'.

Discovery

I discovered my new tree in the spring, 2006, growing in a production area of a liner seedling bed in Belvidere, Franklin County, Tenn., among a group of cultivated Japanese maple trees. These trees were grown from collected seeds planted in 2005.

Propagation

'JN4' was asexually propagated at my direction in the Summer, 2007. The propagation and the resulting progeny have proven the characteristics of my new variety to be firmly fixed. Furthermore, observations have confirmed that my new tree represents a new and improved variety of Japanese Maple tree as particularly evidenced by its persistent red-purple foliage and an early weeping habit, and that my tree can be reliably asexually propagated.

As noted above, my new tree 'JN4' was discovered among a group of Japanese Maple trees. I removed limbs from the tree, took the buds, and chip budded them in the Summer, 2007 at my nursery in Belvidere, Tenn., to asexually reproduce my tree 'JN4' which is now three (3) years old.

Uniqueness

My Japanese Maple tree 'JN4' was observed to have persistent red-purple foliage and an early weeping habit. These characteristics distinguish my new tree from other typical seedling Japanese Maple trees and their known cultivars.

Use

My Japanese Maple tree 'JN4' was observed for a period of time and is believed to be particularly useful anywhere that a Japanese Maple tree is used: as a specimen tree or as an accent tree, or in groupings for a lawn or shrub boarder. It is also widely used for bonsai, and is very effective where an "artistic" touch is needed. Weeping Japanese maple trees are also very useful around water features. A Japanese maple tree with a persistent red-purple foliage and an early weeping habit is also very useful in landscape settings.

BRIEF SUMMARY OF THE INVENTION

The Japanese maple tree, *Acer palmatum*, is native to Japan, China and Korea. For the last century, it has been widely planted in Europe and America. As a species, the Japanese maple tree is highly variable. The species, *Acer palmatum*, is represented by three subspecies and in several forms. There is also an artificial system of groups used for organizing the many named cultivators. My new tree is most correctly described as *Acer palmatum*, subsp. *matsumurae* f. *atropurpureum* in the group *Matsumurae*. An *A. palmatum* subsp. *matsumurae* is delineated by its native habitat, as mentioned below, and its leaf morphology in which the lobes are deeply divided almost to the base of the leaf. The form *atropurpureum* indicates that my new tree is a red-leafed form of the species. In this species, the red leaf color expresses itself in several degrees of red, purple or maroon coloring which can brighten, bronze, or mature to green over the course of a growing season. My new tree is distinguishable in that it has a red-purple leaf color that persists throughout the growing season.

The subspecies *matsumurae* is typically a small tree with a broad-rounded canopy of layered branches which can reach 25 to 30 feet in height with a similar spread. It is native to the mountain forests of Japan and is easily delineated from other subspecies by its lobes that are deeply divided almost to the base of a leaf. The species is found primarily in moist valleys and along streams; and, on the edge of mountain forests at elevations of up to 4000 feet where the soil is moist, well-drained, and acidic. It is intolerant of anaerobic soil conditions and will not grow on flooded sites. The species is an understory tree and is very tolerant of shade and nutrient competition. My new tree has similar dimensions to existing cultivars, while exhibiting a unique weeping habit. However, my new cultivar differs from the species and all known cultivars in that it is an upright grower with red leaves and a weeping habit.

Industry Representation

Cultivated Japanese maple trees are represented in the industry by seedling material and over four hundred cultivars. Many Japanese maple trees are grown from seed, but recently, there has been more interest in the cultivars. Because there are so many cultivars, a brief description of their classifications will be useful and will help illustrate the uniqueness of my new tree. The standard English reference for Japanese maple trees is the 3rd edition of Japanese Maples, by J. D. Vertrees, and his system of classification will be used. There are three subspecies of Japanese maples: a) *A. palmatum* subsp. *palmatum*; b) *A. palmatum* subsp. *amoenum*; and c) *A. palmatum* subsp. *Matsumurae*. The divisions of these subspecies are based on leaf morphology, native habitat, and growth habitat. Within each of these subspecies are several forms and varieties which can cross subspecies boundaries. While this adds some confusion to the nomenclature, it also provides a useful way of organizing this highly variable species. Three important forms of the species exist: a) *f. dissectum*, a small growing, shrub-like form with an ornately dissected leaf; b) *f. atropurpureum*, a red-leafed form of the typically green-leafed species; and, c) *f. dissectum atropurpureum*, a red-leafed form of the shrubbery *f. dissectum*.

There are also seven artificial groups to which cultivars are assigned based mainly on leaf morphology, but sometimes on growth habitat. Those skilled in the art will understand that many of the cultivars possess characteristics of more than one group, and sometimes of more than one subspecies. My new Japanese Maple tree falls into the group *Matsumurae*, which is so named for the subspecies it represents. Although there is no lack of nomenclature and taxonomical grouping, there is still confusion in the trade concerning the proper taxonomy. Another complicating factor is the naming of many cultivars. The species has been in cultivation for over two hundred years, and most of the named selections are from Japan. Since many of the cultivars are Japanese selections, they bear Japanese names which are unfamiliar and sometimes incomprehensible to the American trade. Compounding all of this are the translations, transliterations, localized naming conventions, differing trade names, and typical misspelling errors that occur over a two hundred year period, which means that there are inevitably some naming errors and confusion. Also, in any species represented by some four hundred cultivars, it is to be expected that there are some very similar selections that become mixed up or confused within the trade.

Without exhaustively explaining the differences in each subspecies, form, and group, it is better to describe where my new Japanese Maple tree fits within the extant selections and touch on those cultivars that best illustrate the uniqueness of my new tree. My new tree is of the subspecies *matsumurae*, as distinguished by its leaves which are deeply divided almost to the leaf base. The subspecies is well-represented in the trade. An *A. palmatum* subsp. *matsumurae* has deeply divided leaves with coarser serrations than my tree and tends to be a smaller tree than trees of the other two subspecies. Cultivars of the subspecies, although often described as shrub-like, can still form trees up to thirty feet in height. My new tree is of the form *atropurpureum*, which indicates that it is a red-leafed variety.

Next, it is important to distinguish the upright growth and weeping habit of my new Japanese Maple tree from the shrubby, almost contorted growth of the form *A. palmatum* f. *dissectum*, which also exhibits pendulous branching. The form *dissectum* is so named because of its highly dissected leaves. But, it is also typically a shrubby plant with weeping or cascading branches which, over time, produce a three to five foot high mound of leaves which is described by Vertrees as "a low, spreading shrub." This form, in both its green and red leaf forms, is very popular, but is altogether different form my new tree in both growth habitat and leaf morphology.

There are two upright growing cultivars to which my new tree is similar. One is an *Acer palmatum* 'Omure yama' which is a green leaf form of the *Matsumurae* group that is vigorous and upright as a young plant, but develops weeping branches as it develops into a small round headed tree. The other is *Acer palmatum* 'Oshu shidare' which is a red leaf form of the *Matsumurae* group that has upright branching as a young plant, but develops pendulous branches on the outside of the plant producing a round headed tree with a cascading form. The early upright growth habitat can be seen in this tree as it develops a main trunk and primary branching. The cascading effect only appears later, as the tree matures. The red leaves of the tree are described as red or maroon and develop a greenish cast as they mature. My new tree differs from both 'Omure yama' and 'Oshu shidare' because of its persistent red-purple leaf color (see the first photograph) and because it develops its weeping branching as a young plant (see the second and third photographs).

BRIEF DESCRIPTION OF THE SEVERAL VIEWS OF THE DRAWINGS

The accompanying photographs depict the color of the tree and foliage of my new variety as nearly as is reasonably possible to make the same in a color illustration of this character.

The first photograph depicts summer foliage (RHS 64A); and,

The second and third photographs depict the weeping branching of a young tree.

DESCRIPTION OF THE PREFERRED EMBODIMENT

The following is a detailed description of my new variety of Japanese Maple tree with color terminology in accordance with The Royal Horticultural Society (R.H.S.) colour chart except where the context indicates a term having its ordinary dictionary meaning. My new tree has not been observed under all growing conditions and variations may occur as a result of different growing conditions. All progeny of my new variety of Japanese Maple tree, insofar as they have been observed, are identical in all of the characteristics described below.

Other than as set forth below, as of this time, no other characteristics have been observed which are different from common Japanese maple trees which have been observed by the inventor.

My tree 'JN4', which is three (3) years old, is currently 5' tall, and its branches are 3'-5' long, all of which is typical of the species. As previously noted, my tree has a weeping habit. The diameter of the trunk of the tree is approximately ½" at a height 1 inch above ground level. This is also typical of the species for a tree the age of my tree 'JN4'.

Parentage: Seedling of unknown parentage grown from bare-root liner planted in spring 2005 from collected seed.

Locality where grown and observed: A production seedling bed in Belvidere, Franklin County, Tenn.

Leaves: Typical of the subspecies *matsumurae* f. *atropurpureum* in size, shape and colors: opposite, simple, deeply 5-to-9-lobed. The leaves are lance-ovate to lance-oblong, subcordate, 2 to 5 inches long wide by 2 to 5 inches long; with a red-purple leaf color (RHS 64A) on both sides of a leaf during spring and summer. The lobes are acuminate, doubly serrate. In the species, fall color is highly variable, displaying yellow to orange to red fall color depending on the plant. My new tree has a bright red fall (RHS 42B) color.

Petiole: ¾ to 2 inches long, with a diameter of 1/32 inch to 1/16 inch, and glabrous. My new tree has red-purple (RHS 66A) that is slightly darker than the leaf and typical of the red leaf forms.

Buds: Typical of the species; valvate, small and hidden by the base of the petiole. Buds are ½ "to 1 inch in length, ¼" to ½" at their base, and bright red (RHS 40A). The terminal buds often appear as twins.

Flowers: I have not yet observed flowers on my new tree.

Fruit: I have not yet observed fruit on my new tree.

Stem: Typical of the red leaf forms: slender, glabrous, similar to the petioles in color, but slightly darker on my new tree. The red-leafed cultivars have bright red to purple stems, a trait that persists somewhat as the branches mature. My new tree has reddish purple stems (RHS 71A) typical of the red leaf forms. The length of the stems range are from 2' to 5' and the stem diameter is from 3/16 inch to ½ inch.

Trunk: Typical of the red leaf forms: gray (RHS 197B) infused with red-purple (RHS 71A). Larger red-leaf trees have smooth gray trunks with sinuous branching. Although my tree has not been observed long enough to exhibit this trait, I expect it to be typical of the species. As previously noted, the trunlk of my tree is ½" in diameter 1 inch above the ground.

Branching: Typically upright-spreading. My new tree exhibits a weeping branching pattern early on in its growth which creates a weeping effect. The length of the branches of my tree 'JN4' is 3'-5' which is typical of the species, as is branch diameter which is ¼" to ⅜".

Root System: Japanese Maple trees generally have fibrous root systems which are typical of the genus *Acer.* My new tree has a root system typical of the species.

Growth habit: Weeping, which is rare among upright cultivars. The species is typically a small, spreading tree with a root system typical of the species.

Vigor: Typical of the species. Vigorous if sited in a moist, well-fertilized area. My new Japanese Maple tee has preformed well in the heat and drought experienced in middle Tennessee for each of the last three years. As previously noted, my Japanese Maple tree JN4 is three (3) years old and has attained a height of 5'. In Dirr's Manual of Woody Landscape Plants, Fifth Edition, 1998, he notes on page 28 that the growth rate of an *Acer palmatum* Japanese Maple tree is 10' to 15' over a 10 year period. The growth rate of my Japanese Maple tree JN4 is consistent in this regard.

Diseases: The species has few disease problems. Most disease susceptibility occurs in a greenhouse during propagation when conditions are favorable for the development of a disease. Among the diseases that can affect *A. palmatum* are Verticillium, Fusarium, Botrytis, Pythium, Pseudomonas, Anthracnose, powdery mildew, and various cankers. All of these diseases are generally opportunistic and typically not a problem for a healthy plant. In a nursery, and in landscape settings, diseases are rare. I have not observed any diseases on my new tree or its propagules.

Pests: Japanese Maple trees are in general pest-free; although, Japanese beetles can sometimes cause temporary cosmetic foliar damage. Aphids, mites, various caterpillars and bark beetles, and root weevils are rarely problems. I have observed no pest problems on my new tree or its propagules.

What is claimed is:

1. A new and distinct variety of Japanese Maple tree named 'JN4' substantially as herein shown and described, characterized particularly as to novelty by its persistent red-purple foliage and an early weeping habit.

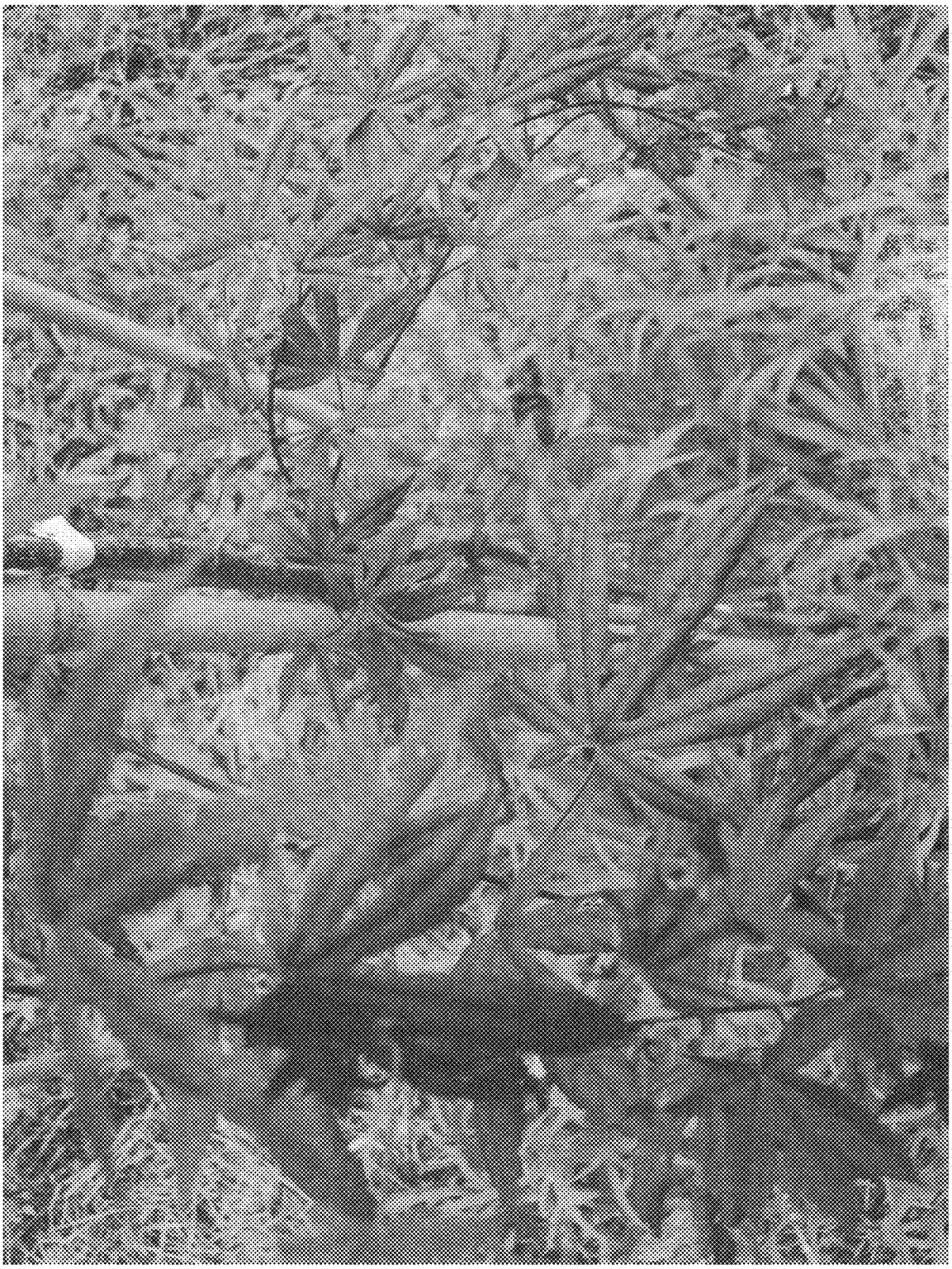

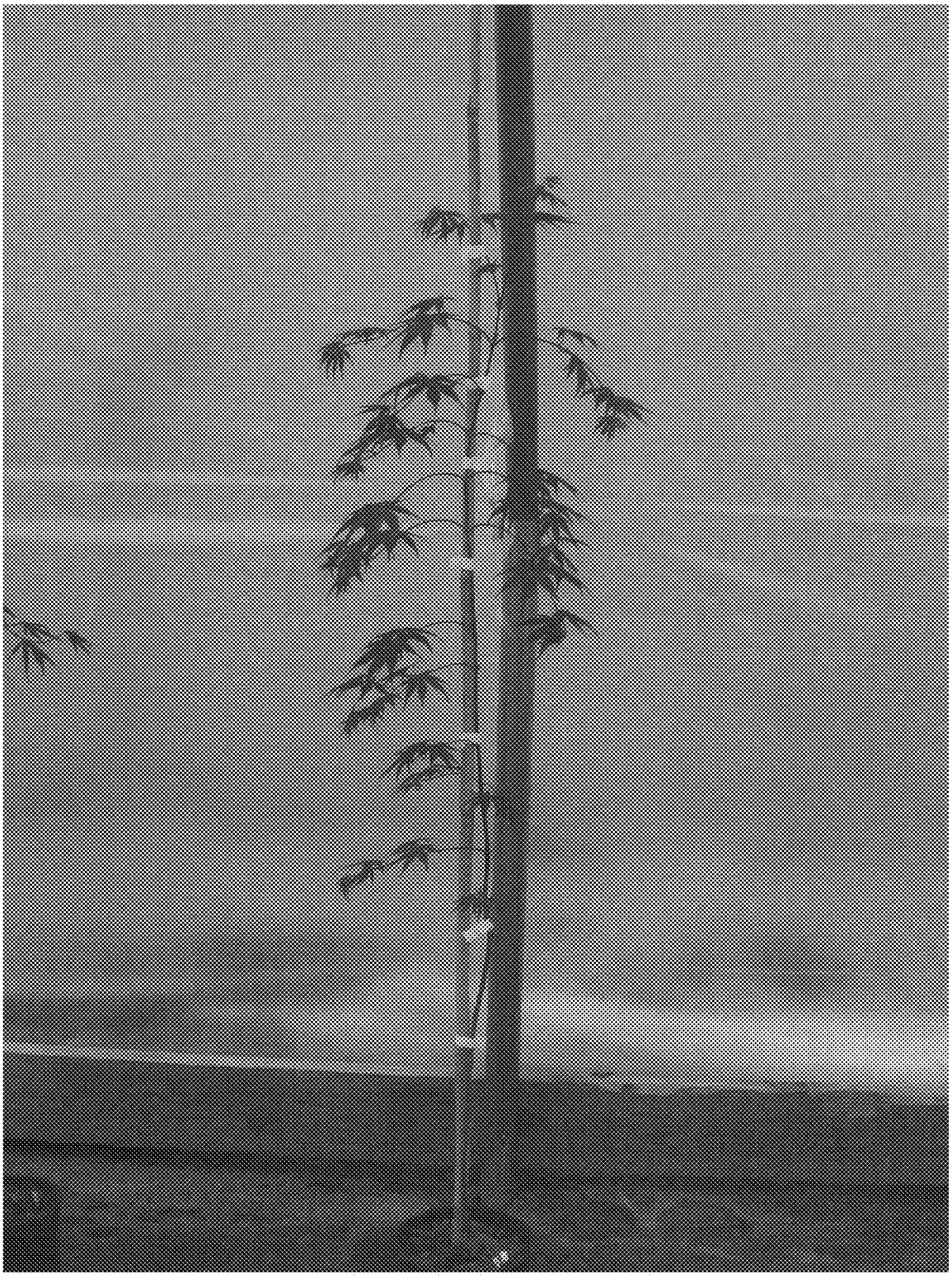

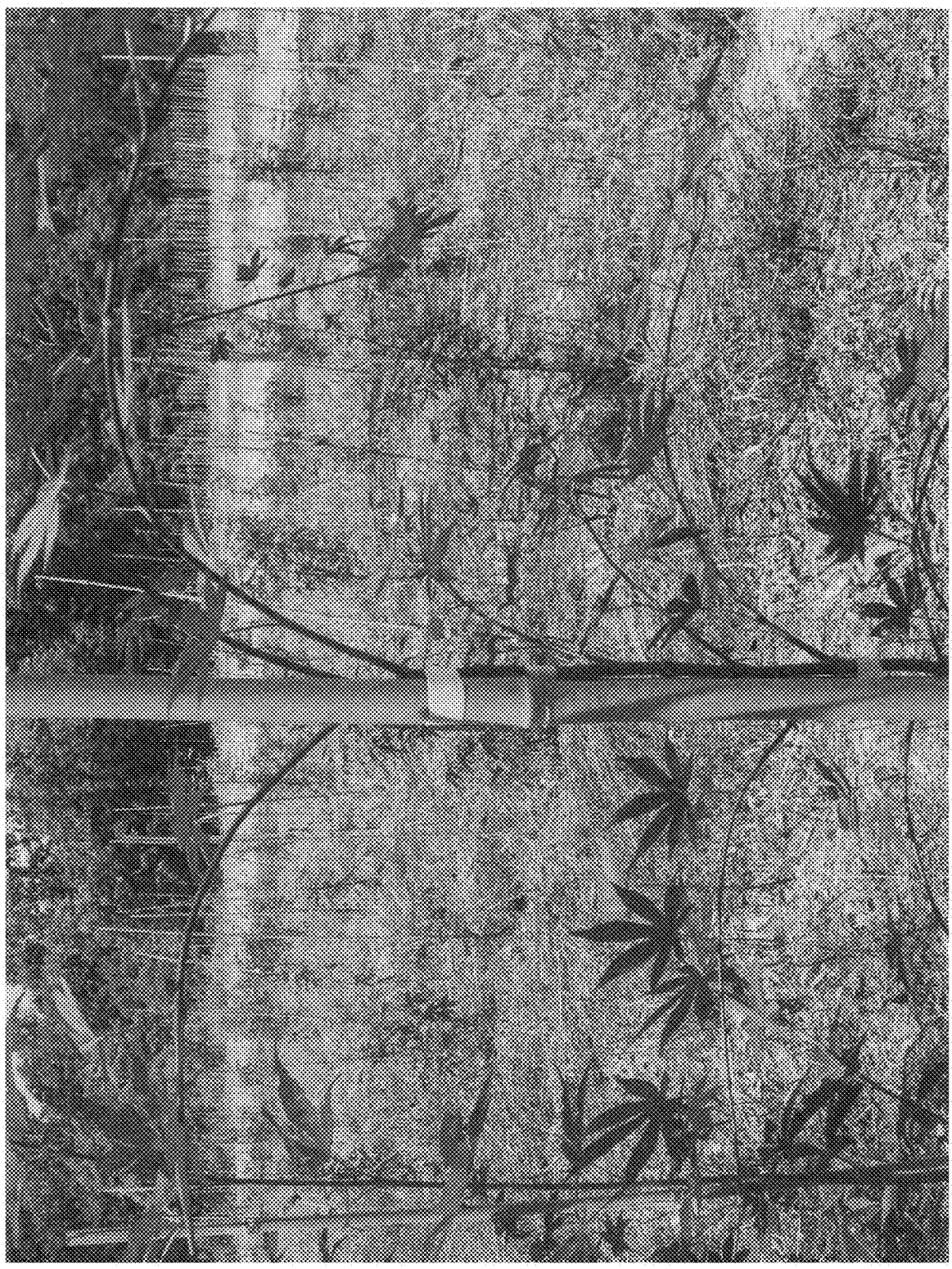

* * * * *